United States Patent [19]

Costello et al.

[11] Patent Number: 5,322,507
[45] Date of Patent: Jun. 21, 1994

[54] ENDOSCOPE FOR TREATMENT OF PROSTATE

[75] Inventors: Anthony J. Costello, Victoria, Australia; William W. Gardetto, Bedford, Tex.; Royice B. Everett, Edmond, Okla.

[73] Assignee: MyriadLase, Inc., Forest Hill, Tex.

[21] Appl. No.: 928,854

[22] Filed: Aug. 11, 1992

[51] Int. Cl.⁵ ............................................. A61B 1/00
[52] U.S. Cl. ........................................ 128/4; 604/27; 604/43
[58] Field of Search ............... 128/3, 4, 6; 604/53, 604/57, 27, 43

[56] References Cited

U.S. PATENT DOCUMENTS

| 3,856,000 | 12/1974 | Chikama | 128/6 |
| 3,858,586 | 1/1975 | Lessen | 128/303.1 |
| 3,911,923 | 10/1975 | Yoon | 128/303 A |
| 4,033,331 | 7/1977 | Guss et al. | 128/2 M |
| 4,076,018 | 2/1978 | Heckele | 128/6 |
| 4,313,431 | 2/1982 | Frank | 128/7 |
| 4,445,892 | 5/1984 | Hussein et al. | 604/101 |
| 4,448,188 | 5/1984 | Loeb | 128/6 |
| 4,470,407 | 9/1984 | Hussein | 128/6 |
| 4,509,507 | 4/1985 | Yabe | 604/27 |
| 4,592,353 | 6/1986 | Daikuzono | 128/303.1 |
| 4,646,737 | 3/1987 | Hussein et al. | 128/303.1 |
| 4,662,368 | 5/1987 | Hussein et al. | 128/303.1 |
| 4,672,963 | 6/1987 | Barkon | 128/6 |
| 4,676,231 | 6/1987 | Hisazumi et al. | 128/6 |
| 4,693,556 | 9/1987 | McCaughan, Jr. | 350/320 |
| 4,736,743 | 4/1988 | Daikuzono | 128/303.1 |
| 4,740,047 | 4/1988 | Abe et al. | 350/96.15 |
| 4,773,413 | 9/1988 | Hussein et al. | 128/303.1 |
| 4,832,979 | 5/1989 | Hoshino | 427/38 |
| 4,858,001 | 8/1989 | Millbank | 128/6 |
| 4,858,595 | 8/1989 | Buess et al. | 128/6 |
| 4,860,743 | 8/1989 | Abela | 128/303.1 |
| 5,041,121 | 8/1991 | Wondrazek et al. | 606/128 |
| 5,074,860 | 12/1991 | Gregory | 128/6 |

FOREIGN PATENT DOCUMENTS

| 525471 | 3/1979 | Japan | 128/6 |
| 14508 | of 1906 | United Kingdom | 128/3 |

OTHER PUBLICATIONS

Article entitled "Nd:YAG Laser Ablation of the Prostate as a Treatment for Benign Prostatic Hypertrophy", Lasers in Surgery and Medicine 12:121-124 (1992).
PCT International Patent Application No. WO 89/11834, published Dec. 14, 1989.
Catalog entitled "The World of Endoscopy: Urology--Endo-Urology", 4th Edition, 1988, published by karl Storz GmbH & Co.

Primary Examiner—Jerome L. Kruter
Attorney, Agent, or Firm—Dougherty, Hessin, Beavers & Gilbert

[57] ABSTRACT

An endoscopic instrument includes a rigid outer sheath having an inner sheath received therein. The outer sheath has a lateral window defined therein near a closed distal end of the outer sheath. The inner sheath carries a telescope and a laterally transmitting laser fiber tip. The laser fiber tip may be extended to a position laterally adjacent the open window while the telescope remains located proximal relative to the tip and the window, so that the tip and the tissue to be treated may be observed with the telescope while both the telescope and the tip remain within the outer sheath.

19 Claims, 2 Drawing Sheets

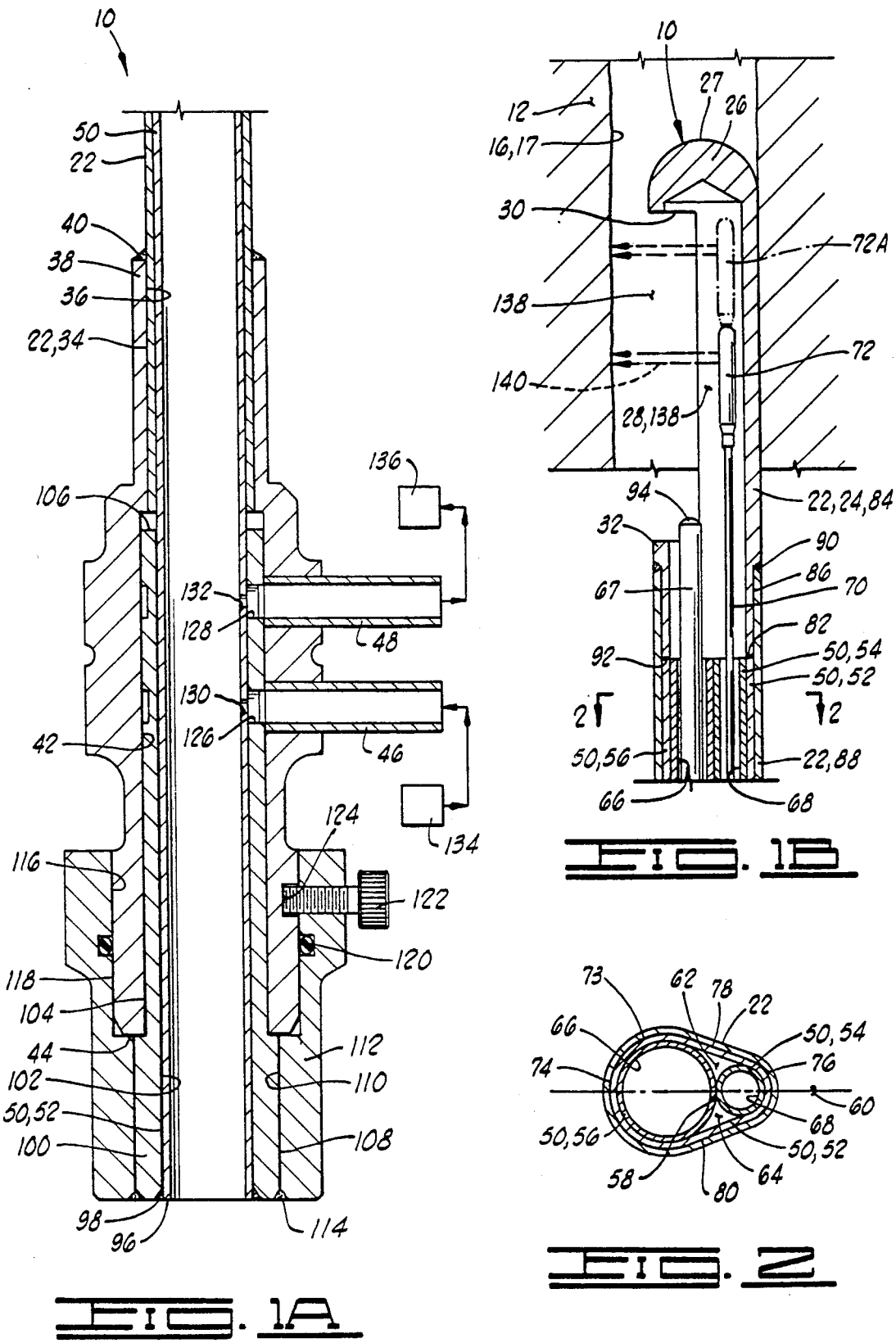

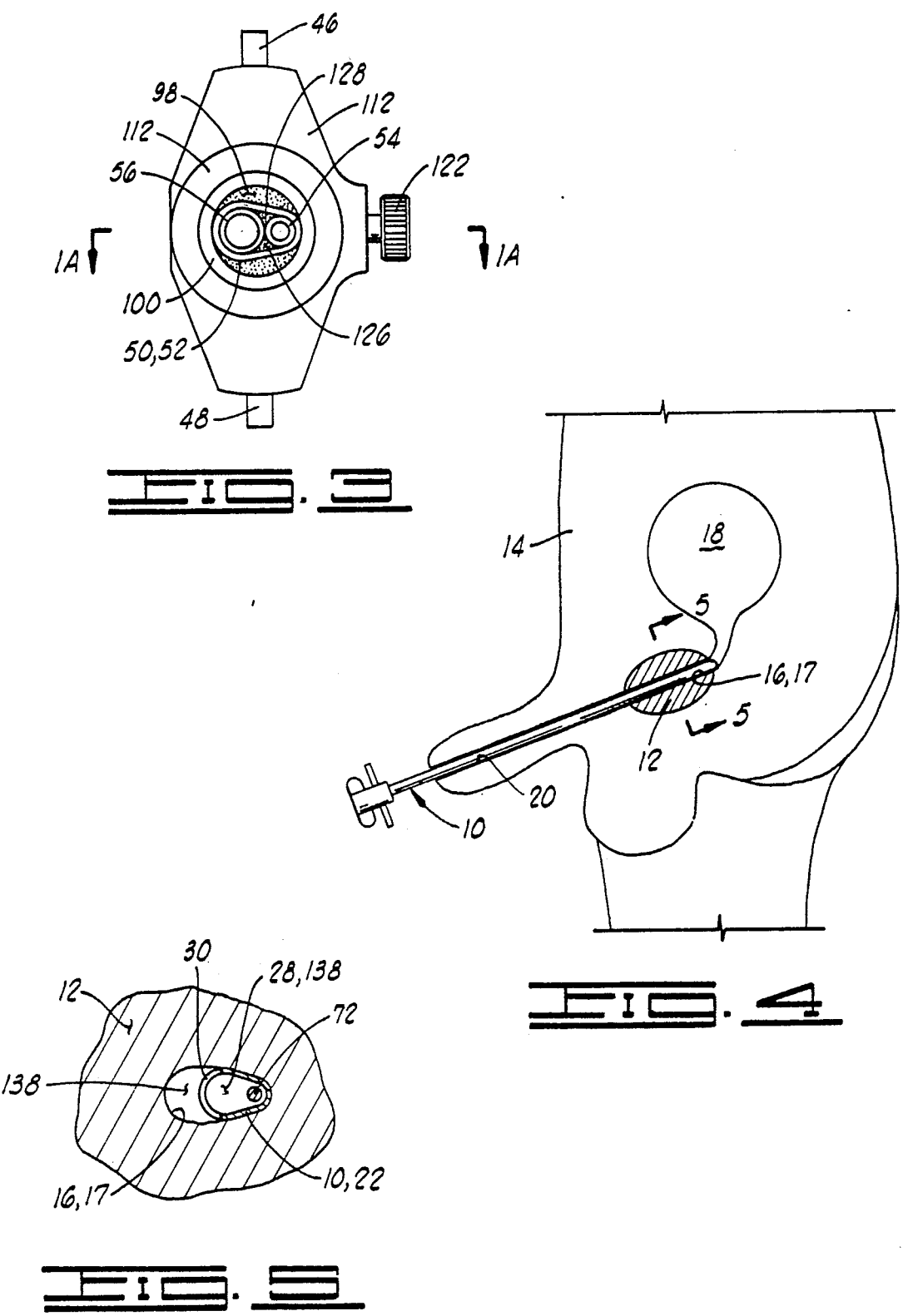

ENDOSCOPE FOR TREATMENT OF PROSTATE

BACKGROUND OF THE INVENTION

1. Field of The Invention

The present invention relates generally to endoscopic apparatus and methods of using the same, and particularly to such apparatus and methods for treatment of the prostate.

2. Description of The Prior Art

It is generally known to use endoscopic apparatus for treatment of urinary tract problems. Typically such devices have been particularly constructed for treatment of the interior of the bladder. Such devices are generally referred to as cystoscopes.

More recently, techniques have been developed using a laterally firing laser for treatment of the prostate, and particularly for treatment of a condition generally known as benign prostatic hypertrophy. This condition involves the swelling of the prostate which tends to close off the prostatic urethra which passes therethrough. In laser treatment of this condition, a laterally firing laser tip is placed within the prostatic urethra and directs a laser beam against the inner wall of the prostate.

To date, such techniques have involved the use of standard cystoscopes which have a number of shortcomings since they were not designed for this usage. A standard cystoscope typically includes a hollow outer tube the distal end of which is open and a lateral portion of which is open and communicated with the open distal end. The laterally firing laser tip is run through the cystoscope and extends out the open end of the cystoscope.

These prior art techniques of laser treatment of benign prostatic hypertrophy are described in Costello et al., "Nd:YAG Laser Ablation of the Prostate as a Treatment for Benign Prostatic Hypertrophy", Lasers in Surgery and Medicine 12:121-124 (1992).

Due to the contracted swollen nature of the prostate when the patient is suffering from benign prostatic hypertrophy, the prostatic urethra therethrough may be essentially completely closed and thus it becomes difficult to place the fiber tip in position to treat the inner wall without having the tip actually engage surrounding tissue. If the tip engages surrounding tissue, this can create difficulties in several ways. If the reflecting surface of the tip touches surrounding tissue, it may become covered with foreign matter so that the tip does not function properly. Also, for maximum operational efficiency, the tip should be spaced from the tissue surface being treated. Also, contact of the tip with tissue while the laser is firing may cause the tip to adhere to the tissue.

SUMMARY OF THE INVENTION

The present invention provides an improved endoscopic apparatus designed especially for use in treating the prostate with a laser beam which is deflected laterally from a tip mounted on the end of a laser transmitting fiber. The endoscopic apparatus includes an outer sheath which provides a means for spreading the prostatic urethra and defining an open space within the prostatic urethra. This outer sheath has a closed distal end and a laterally open window near the closed distal end.

An inner sheath is slidably received within the outer sheath and provides a means for placing a laterally transmitting laser fiber tip within the open space with the tip spaced laterally from a portion of the interior wall of the prostate so that a beam of laser light may be transmitted laterally from the tip through the window of the outer sheath onto that portion of the interior wall of the prostate without touching the interior wall of the prostate with the laterally reflecting laser tip.

Numerous objects, features and advantages of the present invention will be readily apparent to those skilled in the art upon a reading of the following disclosure when taken in conjunction with the accompanying drawings.

BRIEF DESCRIPTION OF THE DRAWINGS

FIGS. 1A-1B together comprise an elevation sectioned view of the endoscopic instrument of the present invention. In FIG. 1A, the lower portions of the internal components carried by the inner sheath are eliminated for purposes of illustration. In FIG. 1B, the internal components are shown and include a telescope and a laser fiber with a laterally transmitting tip in place within the inner sheath.

FIG. 2 is a sectioned view taken along line 2—2 of FIG. 1B illustrating the construction of the inner and outer sheaths. The handle and housing of the lower end of FIG. 1A are eliminated from this view for clarity.

FIG. 3 is a bottom view of the apparatus of FIG. 1A.

FIG. 4 is a schematic illustration of the apparatus of FIGS. 1A-1B in place within a patient's urethra for treatment of the prostate.

FIG. 5 is a schematic sectioned view taken along line 5—5 of FIG. 4 illustrating how the apparatus of FIGS. 1A-1B is used to spread apart the inner walls of the prostate.

DETAILED DESCRIPTION OF THE PREFERRED EMBODIMENTS

FIGS. 1A-1B comprise an elevation sectioned view of an endoscopic instrument generally designated by the numeral 10.

FIG. 4 schematically illustrates the instrument 10 being used to treat the prostate 12 of a human male patient 14. The prostate 12 is an annular gland-like member having an opening through the center thereof which is commonly known as the prostatic urethra 16, which is a part of the urinary tract. The prostate 12 can be described as having an inner wall 17 which defines the prostatic urethra 16 therein. Following the urinary tract further into the patient's body one reaches the bladder 18. Following the urinary tract outward, the prostatic urethra 16 is communicated through the urethra 20 which extends through the penis to the exterior of the patient's body.

The details of construction of the endoscopic instrument 10 are best shown in FIGS. 1A-1B. FIG. 1A comprises a lower portion of the instrument and FIG. 1B comprises the upper portion of the instrument with the FIGS. 1A and 1B being joined along line X—X.

As used herein, the terms proximal and distal are used in their common medical sense wherein the distal end of an instrument is the end which is farther away from the physician and the proximal end of the instrument is the end which is closest to the physician. Thus, the distal end of the instrument 10 is received in the patient's body while the proximal end of the instrument 10 extends from the patient's body and is manipulated by the physician.

The instrument 10 includes a hollow rigid outer sheath 22 having a distal portion 24 with a closed end 26. The distal portion 24 has a hollow space 28 defined therein adjacent the closed end 26. Closed end 26 has a bullet-shaped outer surface 27.

Distal portion 24 also has a lateral window 30 defined therein communicating the hollow space 28 with an exterior 32 of the outer sheath 22.

The outer sheath 22 has a proximal end portion 34 received within a cylindrical bore 36 of a cylindrical housing 38. Outer sheath 22 and housing 38 are fixedly connected together by weld or braze as indicated at 40. As is further explained below, the outer sheath 22 is not circular, and thus there are gaps between sheath 22 and the cylindrical bore 36. The weld 40 is a fill weld which completely fills these gaps so as to seal between the housing 38 and outer sheath 22.

The housing 38 also includes a counterbore 42 which communicates with a proximal end 44 of housing 38.

Housing 38 also has irrigating fluid supply and discharge nipples 46 and 48, respectively, disposed radially therethrough and communicating with the counterbore 42.

As is further described below, the outer sheath 22 and housing 38 provide an outer sheath assembly within which the other components of instrument 10 described below are received in a sliding sword-like fashion.

The instrument 10 also includes an inner sheath 50 which as best seen in FIG. 2 has a laterally enclosed outer wall 52 complementary to and closely received within the outer sheath 22. As is further described below, the inner sheath 50 is so arranged and constructed that the inner sheath 50 and everything contained therein may be withdrawn from the outer sheath 22 while leaving the outer sheath 22 in place within the patient's body. The inner sheath 50 may also be referred to as an inner assembly 50.

As best seen in FIG. 2, the laterally enclosed outer wall 52 of inner sheath 50 is generally pear shaped in cross section. The inner sheath 50 includes a smaller cylindrical tube 54 and a larger cylindrical tube 56 received in outer wall 52. The tubes 54 and 56 laterally abut each other at 58 and they each laterally abut the outer wall 52 along a major axis 60 of the pear-shaped cross section seen in FIG. 2. Thus the laterally enclosed outer wall 52 and the tubes 54 and 56 define first and second interstitial spaces 62 and 64, respectively, therebetween.

The larger tube 56 has a cylindrical tube bore 66 which defines a telescope passage for receiving an optical telescope 67 of the type conventionally used in endoscopic instruments.

The smaller tube 54 has a cylindrical bore 68 which defines a fiber passage or tip passage for receiving a laser light transmitting fiber 70 having a laterally transmitting laser fiber tip 72 mounted thereon.

The laterally firing tip 72 preferably is a SIDEFIRE TM laterally transmitting fiber tip such as is available from MyriadLase, Inc., of Dallas, Tex., and such as is described in detail in U.S. patent application Ser. No. 07/746,418 of Judy et al., filed Aug. 16, 1991, and assigned to the assignee of the present invention. The details of construction of tip 72 as disclosed in application Ser. No. 07/746,418 are incorporated herein by reference.

The first and second interstitial passages 62 and 64 define an irrigating fluid supply passage 62 and an irrigating fluid return passage 64, respectively. As further described below, the supply and return passages 62 and 64 are communicated with the irrigating fluid supply and return nipples 46 and 48, respectively.

The laterally enclosed outer wall 52 can be described as having a perimeter 73 defined by its outer surface seen in the cross section of FIG. 2. The laterally enclosed outer wall 52 can also be described as having a minimum smooth perimetered cross sectional area capable of receiving the tubes 54 and 56 therein, said perimeter 72 including a larger circular portion 74 and a smaller circular portion 76, which are joined by two straight lines 78 and 80.

The inner bore 66 of larger tube 56 preferably has a diameter of slightly greater than five millimeters so that a five-millimeter diameter telescope 67 may be received therethrough. The inner bore 68 of smaller tube 54 preferably has an inner diameter of slightly greater than 2.2 millimeters through which can be received a fiber tip 72 having an outside diameter of 2.2 millimeters. The inner and outer sheaths 50 and 22, and the tubes 54 and 56 contained within inner sheath 50 are all preferably constructed from stainless steel.

Having these dimensions and using relatively thin wall for the outer sheath 22 and inner sheath wall 52, an instrument 10 can be constructed having a cross section as shown in FIG. 2 substantially equivalent in area to that of a size 24 French conventional cystoscope.

The laterally enclosed outer wall 52, the smaller cylindrical tube 54, and the larger cylindrical tube 56, of inner sheath 50 are all fixedly held together by welding as further described below so that the same provide an inner sheath assembly.

As seen in FIG. 1B, the inner sheath 50 has a distal end 82 which terminates short of the window 30 of outer sheath 22. Preferably, the outer sheath 22 is constructed from two parts, namely a distal part 84 having a reduced cross section neck 86 closely received within a proximal tubular part 88 with the two being joined by a weld indicated at 90.

A proximal end 92 of neck 86 defines a shoulder 92 against which the distal end 82 of inner sheath 50 abuts when the inner sheath 50 is fully inserted within the outer sheath 22 as illustrated in FIG. 1B.

As is also seen in FIG. 1B, the fiber passage 68, the telescope passage 66, and the flushing fluid supply and return passages 62 and 64 all have open distal ends adjacent the distal end 82 of inner sheath 50, which open distal ends are all communicated with the hollow space 28 defined within the distal portion 24 of outer sheath 22.

As seen in FIG. 1B, the fiber passage or tip passage 68 is located on a lateral side of inner sheath 50 opposite the window 30 of outer sheath 22, so that when the laser fiber tip 72 is inserted into the hollow space 28, the laser fiber tip 72 is laterally spaced from the window 30 as seen in FIGS. 1B and FIG. 5. As is further described below, this lateral spacing helps prevents the tip 72 from actually touching the inner wall 17 of the prostatic urethra 16 of prostate 12.

The telescope passage 66 is located on a lateral side of the inner sheath 50 adjacent the window 30 so that when the telescope 67 is extended distally out of the open end 82 of inner sheath 50, the telescope 67 will be as close as possible to the window 30. The telescope 67 may have a lens 94 defined on the distal end thereof so that the telescope 67 allows the physician to look out the window 30 and observe the area of inner wall 17 being treated by a laser light beam transmitted from tip 72. The lens 94 may for example be a 30° diverging view lens. The tip 72 may also be viewed with the telescope 67 since the distal end 94 of telescope 67 is located proximally of the laser fiber tip 72 as illustrated in FIG. 1B.

The window 30 is open through an arc of approximately 180° about a longitudinal axis of the outer sheath 22. Preferably, the window 30 is constructed to correspond to an arc of 180° about the longitudinal central axis of larger tube 56 when the inner sheath 50 is in place within the outer sheath 22.

The inner sheath 50 has a proximal end 96 seen at the bottom of FIG. 1A. Inner sheath 50 is connected at its proximal end 96 by a weld 98 to an intermediate cylindrical tube 100. The tube 100 has a cylindrical bore 102 having a diameter just slightly larger than the maximum cross-sectional dimension of the cross-sectional area of outer wall 52 seen in FIG. 2 along the major axis 60.

The weld 98 is a fill weld which will seal between the outer surface of outer wall 52 and the bore 102 of intermediate cylindrical tube 100.

The intermediate cylindrical tube 100 has a reduced diameter cylindrical outer surface 104 which is closely received within counterbore 42 of cylindrical housing 38. The intermediate cylindrical tube 100 has a distal end 106.

Intermediate cylindrical tube 100 includes a larger diameter cylindrical outer surface 108 which is closely received within a bore 110 of a handle 112. The intermediate cylindrical tube 100 and handle 112 are fixedly joined together by weld 114. Thus, the handle 112, intermediate cylindrical member 100 and inner sheath 50 are all fixedly connected together and may be withdrawn together from engagement with the housing 38 and outer sheath 22.

The handle 112 has a counterbore 116 which is closely received about a cylindrical outer surface 118 of housing 38 with a sliding O-ring seal 120 being provided therebetween. Handle 112 carries a threaded set screw 122 which may be received within a blind bore 124 of housing 38 to fix the inner sheath 50 in position within the outer sheath 52. When it is desired to withdraw the inner sheath 50, the set screw 122 is loosened until it is withdrawn from blind bore 124 and then the inner sheath 50 may be withdrawn from outer sheath 22.

As seen in FIG. 3, the handle 112 has eccentric ears thereon to allow the physician to insert and transmit torque to the instrument 10 to axially and rotationally manipulate it within the body cavity.

As best seen in FIG. 3, the proximal ends of larger tube 56 and smaller tube 54 are open. The interstitial passages 62 and 64 are closed by fill welds 126 and 128.

In FIG. 1A, the irrigation fluid supply and discharge nipples 46 and 48 are schematically illustrated and are rotated out of their normal positions so that they may be illustrated in the plane of FIG. 1A. Actually, the supply and discharge nipples 46 and 48 are each rotated approximately 90° in opposite directions from the plane of FIG. 1A so that they are oriented in the positions generally seen in FIG. 3. Also, the intermediate cylindrical member 100 has first and second ports 126 and 128 defined therethrough which are aligned with the bores of nipples 46 and 48 and with ports 130 and 132 defined through the outer wall 52 of inner sheath 50. The ports 126 and 130 are of course actually aligned with the supply passage 46 seen in FIG. 3, and the ports 128 and 132 are actually aligned with the return nipple 48 seen in FIG. 3.

Also, to seal between the supply nipple 46 and return nipple 48, there is another fill weld (not shown), similar in shape to fill weld 98 seen in FIG. 3, which is located longitudinally between nipples 46 and 48 and seals between the outer surface of inner sheath 50 and the bore 102 of intermediate cylindrical member 100 to separate the fluid supply and return passages.

The fluid supply nipple 46 provides irrigating fluid from a fluid source 134. The fluid return nipple returns irrigating fluid from the patient's body to a fluid dump zone 136 external of the patient's body.

SURGICAL METHODS OF PROSTATE TREATMENT

The methods of using the apparatus 10 are best described with reference to FIGS. 4 and 5. Although these methods were developed initially for treatment of Benign Prostatic Hypertrophy, they may also be used to treat other diseases such as prostate cancer.

Either the outer sheath 22 alone, or the entire apparatus 10 including the outer sheath 22 with the inner sheath 50 received therein is transurethrally inserted within the patient. That is, it is inserted through the urethra 20 and into the prostatic urethra 16 to a position generally like that shown in FIG. 4.

Preferably, the apparatus 10 is inserted as an assembly with the telescope 67 and laser fiber 70 already in place within the telescope passage 66 and laser fiber passage 68. It will be understood, however, that the telescope 67 and laser fiber 70 may be inserted into the telescope passages 66 and 68 after the apparatus 10 is in place. Also, the outer sheath 22 may first be placed within the patient, and then the inner sheath 50 with the telescope 67 and laser fiber 70 may be inserted into the outer sheath 22. Also, the inner sheath may be inserted into the outer sheath and then the laser fiber 70 and telescope 67 may be inserted in place within the inner sheath.

In any event, the laser fiber 70 is transurethrally placed within the patient's prostatic urethra 16, and this is accomplished without touching the laterally transmitting tip 72 to any of the patient's tissue including the inner wall 17 of the prostatic urethra 16.

The instrument 10, and particularly the outer sheath 22 thereof, is then used to spread opposed portions of the inner wall 17 thereby defining an open space 138 within the patient's prostatic urethra. As is apparent in FIG. 5, the hollow space 28 within the outer sheath 22 may be considered to be a part of the open space 138 between the opposed portions of the inner wall 17 of prostatic urethra 16 This spreading motion is accomplished by pushing laterally with the rigid instrument 10.

As best seen in FIG. 5, the laterally transmitting tip has been placed within the open space 138 adjacent the window 30 of outer sheath 22.

As best seen in FIG. 1B, the laterally transmitting tip 72 is located proximally of the end wall 26, and the lens 94 of telescope 67 is located proximally of the tip 72 while both the telescope 67 and tip 72 are contained within the outer sheath 22 and protected from contact with the patient's bodily tissues.

The tip 72 is oriented so that a laser light beam 140 transmitted therefrom passes through the window 30 and falls on the inner wall 17 to treat the patient's prostate 12.

During this treatment, the telescope 67 may be used to visualize both the area of inner wall 17 being treated, and the laterally transmitting tip 72.

If at any time during the procedure, there is a need to clean or withdraw either the telescope 67 or laterally transmitting tip 72, this can be easily accomplished by withdrawing the entire inner sheath 50 and everything contained therein from the outer sheath 22 while leaving the outer sheath 22 in place. Then the telescope and/or fiber tip 72 may be cleaned or replaced as necessary and the assembly reinserted within the outer sheath 22 after which the operation can continue.

During the operation, irrigating fluid from source 134 is provided through the irrigating fluid supply passage 62 and exits the end thereof proximally from the location o laterally transmitting tip 72 thus providing a flow of clean irrigating fluid over the tip 72 which aids in keeping the tip 72 clean and aids in preventing significant heating of the tip 72. Excess irrigating fluid within the space 138 may simultaneously return through return passage 64. Thus, a continuous stream of irrigating fluid is provided across the tip 72 throughout the operating procedure.

The closed distal end 26 of outer sheath 22 prevents the tip 72 from extending out of outer sheath 22 when the tip 72 is being moved longitudinally within outer sheath 22.

As is apparent in FIG. 1B, the window 30 preferably has a longitudinal length several times that of the longitudinal length of tip 72 so that the tip 72 may be longitudinally moved to a plurality of positions such as the second position 72A shown in phantom lines, while maintaining the window 30 in the same position relative to the patient. Then the tip in position 72A can again transmit a laser light beam onto the inner wall 17 at a location longitudinally spaced from the location treated during the initial treatment illustrated in the solid line position 72 of FIG. 1B. This is particularly advantageous when the contracted portion of the prostatic urethra 16 is longer than normal and it is desirable to treat the tissue at more than one longitudinal position to open the entire length of the prostatic urethra.

The operating technique may include a series of rotationally positioned treatments as described in Costello et al. "Nd:YAG Laser Ablation of the Prostate as a Treatment for Benign Prostatic Hypertrophy", Lasers in Surgery and Medicine 12:121-124 (1992), with the fiber tip 72 held stationary during treatment. Alternatively, the apparatus 10 having the elongated window 30 several times the length of laterally transmitting tip 72 allows the tip 72 to be longitudinally reciprocated back and forth during the firing of the laser so as to uniformly treat an elongated strip of the inner wall 17 of the prostatic urethra 16. This can be done at several rotational orientations to treat the entire prostate.

The inner sheath 50 may be generally described as a means for placing the laterally transmitting fiber tip 72 within the open space 138 with the tip 72 spaced laterally from a portion of the inner wall 17 which is to be treated, so that a beam of laser light 140 may be transmitted laterally from the tip 72 to the inner wall 17 without the tip 72 ever touching the interior wall 17.

The apparatus and methods described above provide several advantages to prior art techniques, and particularly they provide several advantages as compared to the techniques discussed in Costello et al. "Nd:YAG Laser Ablation of the Prostate as a Treatment for Benign Prostatic Hypertrophy", Lasers in Surgery and Medicine 12:121-124 (1992). That prior art technique as illustrated in FIG. 2 of the Costello et al. article involves the longitudinal movement of the laterally reflecting tip to a position far distal from the distal end of the outer sheath of a conventional cystoscope. Thus, the laterally reflecting tip necessarily touches the patient's tissue and may become contaminated. Most significantly, foreign matter may impair the reflectivity of the mirror contained in the tip so that the tip does not fully reflect the laser light coming down the laser transmitting fiber. If the mirror is blocked with foreign matter, this can result in the destruction of the tip through overheating.

Also, although the outer sheath shown in the Costello et al. article can be used to laterally press against the inner wall of the prostatic urethra, it does so at a position considerably proximal from the operating location of the reflecting tip.

Thus it is seen that the apparatus and methods of the present invention readily achieve the ends and advantages mentioned as well as those inherent therein. While certain preferred embodiments of the invention have been illustrated and described for purposes of the present disclosure, numerous changes may be made by those skilled in the art which change are encompassed within the scope and spirit of the present invention as defined by the appended claims.

What is claimed is:

1. An endoscopic instrument apparatus for use in treating a patient's prostate, said prostate having an interior wall defining a prostatic urethra, comprising:
    means for spreading said prostatic urethra and defining an open space within said prostatic urethra; and
    means for placing a laterally transmitting laser fiber tip within said open space with said tip spaced laterally from a portion of said interior wall so that a beam of laser light may be transmitted laterally from said tip to said portion of said interior wall without touching said interior wall with said tip; and
    wherein said means for spreading includes a rigid outer sheath constructed to be received through the patient's urethra, said outer sheath having a distal end portion constructed to be received in the patient's prostatic urethra and to hold said prostatic urethra open and define said open space at least partially within said outer sheath, said outer sheath having an open lateral window defined therein communicating said open space with said prostatic urethra.

2. The apparatus of claim 1, wherein:
    said outer sheath has a closed distal end.

3. The apparatus of claim 2, wherein:
    said distal end of said outer sheath has a bulletshaped outer surface.

4. The apparatus of claim 1, wherein:
    said means for placing includes an inner assembly closely received in said outer sheath, said inner assembly being so arranged and constructed that said inner assembly and everything contained therein may be withdrawn from said outer sheath while leaving said outer sheath in place within the patient's urethra and the patient's prostatic urethra.

5. The apparatus of claim 4, wherein said inner assembly has defined therein:
    a tip passage for receiving said laterally transmitting laser fiber tip; and
    a telescope passage for receiving a telescope.

6. The apparatus of claim 5, wherein:

said inner assembly has a pear-shaped cross section with an outer wall and has a larger cylindrical tube and a smaller cylindrical tube received therein, said tubes laterally abutting each other and said outer wall along a major axis of said pear-shaped cross section, and said outer wall and said tubes defining first and second interstitial spaces therebetween, said larger cylindrical tube defining said telescope passage, said smaller cylindrical tube defining said tip passage, and said interstitial spaces defining an irrigating fluid supply passage and an irrigating fluid return passage.

7. The apparatus of claim 5, wherein:

said inner assembly has a distal end which terminates short of said window; and said tip passage and said telescope passage have open distal ends communicated with said open space.

8. The apparatus of claim 5, wherein:

said tip passage is located on a lateral side of said inner sheath opposite said window of said outer sheath so that when said laser fiber tip is extended from said inner assembly into said open space, said laser fiber tip is laterally spaced from said window.

9. The apparatus of claim 5, wherein:

said telescope passage is located on a lateral side of said inner assembly adjacent said window.

10. The apparatus of claim 1, wherein:

said window is open through an arc of at least about 180°.

11. The apparatus of claim 1, wherein:

said window has a length at least twice a length of said laser fiber tip.

12. An endoscopic instrument apparatus, comprising:

a hollow rigid outer sheath having a distal portion with a distal end, said distal portion having a hollow space defined therein adjacent said distal end and having a lateral window defined therein communicating said hollow space with an exterior of said outer sheath;

an inner sheath having a laterally enclosed outer wall complementary to and closely received within said outer sheath, said inner sheath being so arranged and constructed that said inner sheath and everything contained therein may be withdrawn from said outer sheath while leaving said outer sheath in place within a patient's body, said inner sheath having defined therein:

a tip passage for receiving a laterally transmitting laser fiber tip;

a telescope passage;

an irrigating fluid supply passage; and an irrigating fluid return passage;

wherein said inner sheath has a distal end which terminates short of said window; and wherein said tip passage, said telescope passage, said supply passage and said return passage all have open distal ends communicated with said hollow space of said outer sheath.

13. The apparatus of claim 12 wherein:

said laterally enclosed outer wall of said inner sheath is pear shaped in cross section, and said inner sheath includes a smaller cylindrical tube and larger cylindrical tube received therein, said tubes laterally abutting each other and said outer wall along a major axis of said pear-shaped cross section, said outer wall and said tubes defining first and second interstitial spaces therebetween, said larger tube defining said telescope passage, said smaller tube defining said fiber tip passage, and said interstitial spaces defining said supply passage and said return passage.

14. The apparatus of claim 12, wherein:

said tip passage is located on a lateral side of said inner sheath opposite said window of said outer sheath, so that when said laser fiber tip is extended from said inner sheath into said hollow space, said laser fiber tip is laterally spaced from said window.

15. The apparatus of claim 12, wherein:

said telescope passage is located on a lateral side of said inner sheath adjacent said window.

16. The apparatus of claim 12, in combination with said laterally transmitting laser fiber tip, wherein:

said window has a length at least twice a length of said tip.

17. The apparatus of claim 12, wherein:

said window is open through an arc of about 180° around a longitudinal axis of said outer sheath.

18. The apparatus of claim 12, wherein:

said distal end is a closed distal end.

19. An endoscopic instrument apparatus for use in treating a patient's prostate, said prostate having an interior wall defining a prostatic urethra, comprising:

means for spreading said prostatic urethra and defining an open space within said prostatic urethra; and means for placing a laterally transmitting laser fiber tip within said open space with said tip spaced laterally from a portion of said interior wall so that a beam of laser light may be transmitted laterally from said tip to said portion of said interior wall without touching said interior wall with said tip;

wherein said means for spreading includes a rigid outer sheath constructed to be received through the patient's urethra, said outer sheath having a distal end portion constructed to be received in the patient's prostatic urethra and to hold said prostatic urethra open and define said open space at least partially within said outer sheath, said outer sheath having a lateral window defined therein communicating said open space with said prostatic urethra;

wherein said means for placing includes an inner assembly closely received in said outer sheath, said inner assembly being so arranged and constructed that said inner assembly and everything contained therein may be withdrawn from said outer sheath while leaving said outer sheath in place within the patient's urethra and the patient's prostatic urethra; and said inner assembly has an open distal end which communicates with said open space.

* * * * *